(12) United States Patent
Wang et al.

(10) Patent No.: US 10,743,816 B2
(45) Date of Patent: Aug. 18, 2020

(54) BLOOD PRESSURE TESTING DEVICE

(71) Applicant: BOE Technology Group Co., Ltd., Beijing (CN)

(72) Inventors: Zifeng Wang, Beijing (CN); Yan Ren, Beijing (CN); Lei Cao, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 38 days.

(21) Appl. No.: 15/918,505

(22) Filed: Mar. 12, 2018

(65) Prior Publication Data
US 2019/0125265 A1 May 2, 2019

(30) Foreign Application Priority Data

Oct. 26, 2017 (CN) .......................... 2017 1 1014063

(51) Int. Cl.
A61B 5/00 (2006.01)
A61B 5/0408 (2006.01)
(Continued)

(52) U.S. Cl.
CPC ............ *A61B 5/6826* (2013.01); *A61B 5/021* (2013.01); *A61B 5/024* (2013.01); *A61B 5/0205* (2013.01);
(Continued)

(58) Field of Classification Search
None
See application file for complete search history.

(56) References Cited

U.S. PATENT DOCUMENTS 5,188,115 A 2/1993 Otani
5,511,546 A 4/1996 Hon
(Continued)

FOREIGN PATENT DOCUMENTS

| CN | 1486674 A | 4/2004 |
| CN | 1830382 A | 9/2006 |
| TW | I527562 B | 4/2016 |

OTHER PUBLICATIONS

Office Action, including Search Report, for Chinese Patent Application No. 201711014063.2, dated Nov. 28, 2019, 12 pages.

*Primary Examiner* — Brian T Gedeon
(74) *Attorney, Agent, or Firm* — Westman, Champlin & Koehler, P.A.

(57) ABSTRACT

A blood pressure testing device for a finger is provided in the embodiments of the disclosure, including: a housing; at least one cover plate connected pivotably to the housing; at least one detecting element, each of which is configured to detect an electrocardiogram signal and a pulse signal, and arranged to be accommodated within and connected with the housing and provided opposite to a corresponding one of the at least one cover plate so as to cooperate to define collectively a testing hole therebetween; and at least one adjusting component, each of which is arranged to be connected with the corresponding one of the at least one cover plate, and configured to drive the corresponding one of the at least one cover plate to carry out one of operations comprising: lifting up to move away from a corresponding one of the at least one detecting element, and falling down to approach the corresponding one of the at least one detecting element.

17 Claims, 3 Drawing Sheets

(51) Int. Cl.
    *A61B 5/0205*     (2006.01)
    *A61B 5/021*     (2006.01)
    *A61B 5/024*     (2006.01)

(52) U.S. Cl.
    CPC ....... *A61B 5/02438* (2013.01); *A61B 5/04085* (2013.01); *A61B 5/7278* (2013.01)

(56) References Cited

U.S. PATENT DOCUMENTS

| | | |
|---|---|---|
| 7,572,229 B2 | 8/2009 | Yeo et al. |
| 2004/0024326 A1 | 2/2004 | Yeo et al. |
| 2008/0306395 A1* | 12/2008 | Xu ..................... A61B 5/02416 600/509 |

\* cited by examiner

BLOOD PRESSURE TESTING DEVICE

CROSS-REFERENCE TO RELATED INVENTION

The present disclosure claims the benefit of Chinese Patent Application Invention No. 201711014063.2 filed on Oct. 26, 2017 in the State Intellectual Property Office of China, the whole disclosure of which is incorporated herein by reference.

BACKGROUND OF THE INVENTION

Field of the Invention

Embodiments of the present disclosure relate to the technical field of blood pressure testing, and especially to a blood pressure testing device.

Description of the Related Art

In the prior art, by way of example, a common blood pressure testing device may for example be one of the following: a shoulder-mounted type, a wrist-watch type, and so on. A blood pressure testing device of the shoulder-mounted type is typically of a relatively large volume and may apply a relatively high pressure on both an arm and a shoulder of a user during test, and requires that the user may not wear too much excessive clothing on the arm and the shoulder so as to ensure accuracy of tested data acquired thereby. And a blood pressure testing device of the wrist-watch type is a relatively burgeoning research direction in the technical field of wearable device, with a working principle of implementing a measurement on specific value of blood pressure by pressing against three different electrodes with both hands; specifically, this method requires the user presses against electrodes at three locations with both hands for about one minute. In other words, during this course, it is required to maintain a voluntary pressing with the fingers on both hands, persistently. Since during this course of measurement, fingers of one hand maintains pressing against the wrist-watch type blood pressure testing device worn on the other hand; thus the user's experience may be impaired by a persistently uneven force-application and force-bearing thus caused.

SUMMARY OF THE INVENTION

The embodiments of the present disclosure have been made to overcome or alleviate at least one aspect of the above mentioned disadvantages and/or shortcomings in the prior art, by providing a blood pressure testing device.

Following technical solutions are adopted in exemplary embodiments of the invention for achieving the above desired technical purposes.

According to an aspect of the exemplary embodiment of the present disclosure, there is provided a blood pressure testing device for a finger, comprising: a housing; at least one cover plate connected pivotably to the housing; at least one detecting element, each of which is configured to detect an electrocardiogram signal and a pulse signal, and arranged to be accommodated within and connected with the housing and provided opposite to a corresponding one of the at least one cover plate so as to cooperate to define collectively a testing hole therebetween; and at least one adjusting component, each of which is arranged to be connected with the corresponding one of the at least one cover plate, and configured to drive the corresponding one of the at least one cover plate to carry out one of operations comprising: lifting up to move away from a corresponding one of the at least one detecting element, and falling down to approach the corresponding one of the at least one detecting element.

BRIEF DESCRIPTION OF THE DRAWINGS

The above and other features and advantages of the present disclosure will become more apparent and a more comprehensive understanding of the present disclosure can be obtained, by describing in detail exemplary embodiments thereof with reference to the accompanying drawings, in which.

DETAILED DESCRIPTION OF EMBODIMENTS OF THE INVENTION

Figure 1:
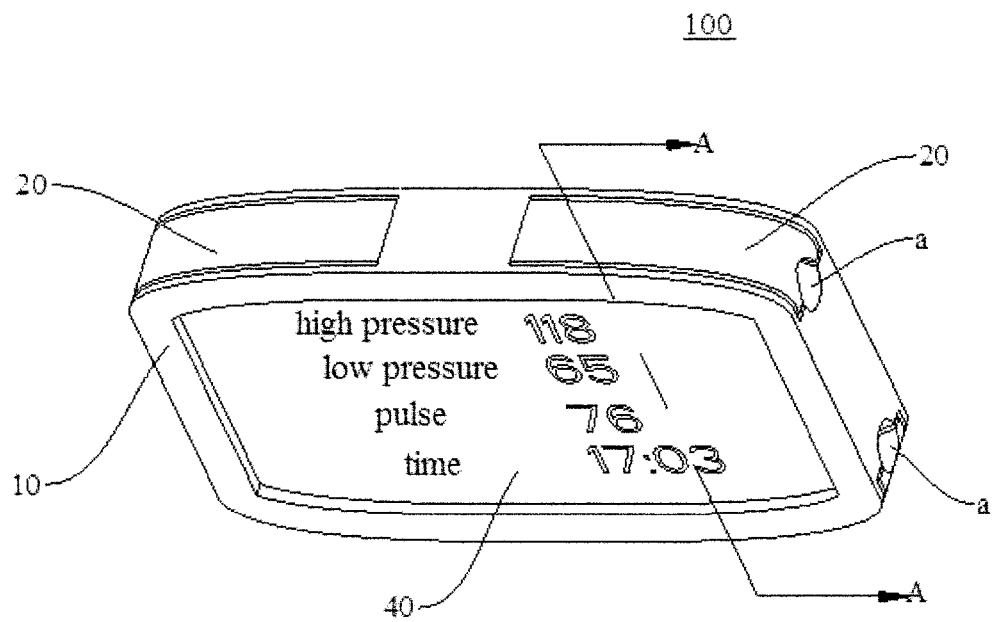
FIG. 1 illustrates a perspective view of the blood pressure testing device in an exemplary embodiment of the disclosure.

Exemplary embodiments of the present disclosure will be described hereinafter in detail with reference to the attached drawings, wherein the like reference numerals refer to the like elements. The present disclosure may, however, be embodied in many different forms, and thus the detailed description of the embodiment of the disclosure in view of attached drawings should not be construed as being limited to the embodiment set forth herein; rather, these embodiments are provided so that the present disclosure will be thorough and complete, and will fully convey the general concept of the disclosure to those skilled in the art.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In depiction of the embodiments of the disclosure, it should be comprehended that, any orientative or positional relationship indicated by terminologies "central", "longitudinal", "transverse", "length", "width", "thickness", "upper", "lower", "front", "back", "left", "right", "vertical", "horizontal", "top", "bottom", "inner", "outer" and so on is based on orientative or positional relationship as illustrated in accompanied drawings, only intending to facilitate and simplify depictions of embodiments of the disclosure, rather than indicating or implying that such referred device or element should necessarily have a specific orientation, or be constructed in a specific orientation or operate in a specific orientation, therefore, such terminologies should not be comprehended as limitations to embodiments of the disclosure.

Besides, terminologies "first", "second" may only intend to be used for depiction, rather than intending to be comprehended to indicate or imply relative importance or to indicate impliedly specific number of technical features as mentioned. Thereby, features defined by "first", "second" may comprise explicitly or impliedly one or more such features. In depictions of embodiments of the disclosure, an expression "a plurality of/the plurality of" means at least two, such as two, three, etc., unless it is defined otherwise definitely.

By referring to FIGS. 1 to 4, there is depicted a blood pressure testing device 100 according to embodiments of the disclosure.

According to a general technical concept of embodiments of the present disclosure, as illustrated in FIG. 1, there is provided a blood pressure testing device 100 according to an embodiment of the disclosure, comprising: a housing 10; at least one cover plate 20 connected pivotably to the housing 10; at least one detecting element 50, each of which is configured to detect an electrocardiogram signal and a pulse signal, and arranged to be accommodated within and connected with the housing 10, and provided opposite to a corresponding one of the at least one cover plate 20 so as to cooperate to define collectively a testing hole labeled 'a' therebetween; and at least one adjusting component 30, each of which is arranged to be connected with the corresponding one of the at least one cover plate 20, and configured to drive the latter to carry out one of operations comprising: lifting up to move away from a corresponding one of the at least one detecting element 50, and falling down to approach the corresponding one of the at least one detecting element 50.

In the blood pressure testing device 100 according an embodiment of the disclosure, the at least one cover plate 20 may be provided, which may be controlled by the at least one adjusting component 30 to lift up or fall down, such that both the corresponding one of the at least one cover plate 20 and the corresponding one of the at least one detecting element 50 cooperate with each other to define the testing hole 'a' whose size may be adjustable. As such, when a finger of a user is inserted into the testing hole 'a', the corresponding adjusting component 30 drives the corresponding cover plate 20 to move towards the corresponding detecting element 50 such that a size of the testing hole 'a' is shrunken/decreased, so as to press the finger accommodated therein gradually against the corresponding one of the at least one detecting element 50. In this way, in the course of detection, it is not required for the user to press on the finger to be detected voluntarily for a long time; alternatively, the corresponding adjusting component 30 may press the finger against the detecting element 50, with the corresponding cover plate 20, by adapting the position of the corresponding cover plate 20 timely, not only enhancing feeling of comfort in experience during testing but also facilitating a more uniform force bearing on the finger and a more accurate result of the detection during a course of signal acquisition by the detecting element 50.

According to embodiments of the disclosure, each of the at least one adjusting component 30 is configured to: drive the corresponding one of the at least one cover plate 20 to fall down gradually so as to press tightly against the finger, as the finger is inserted deeper into the testing hole 'a', before being tested; and drive the corresponding one of the at least one cover plate 20 to lift up gradually so as to release the finger as the finger is removed from the testing hole 'a', after being tested.

In other words, one adjusting component 30 may for example adjust a degree of falling of the corresponding cover plate 20 depending on a specific depth of the finger being inserted into the testing hole 'a', and may be lifted up automatically as the finger is pulled out during removal of the finger after testing.

Specifically, since each one of fingers of a person is tapered towards a tip thereof, i.e., with a relatively thick root and a relatively slim tip end, and sizes of fingers differ from person to person, then, by a single inserting action of one finger before testing, the adjusting component 30 may adjust a distance between the adjusting component 30 and a corresponding detecting element depending on depth of insertion by the finger. In other words, different depths of insertion by the finger within the testing hole 'a' may be adapted for different sizes of the fingers to be detected. The deeper a finger inserts, the smaller the distance between the corresponding cover plate 20 and the corresponding detecting element 50 may be obtained by adjustment of the adjusting component. The adjusting component 30 may hereby adjust automatically a degree in which the corresponding cover plate 20 is pressed downward, for example, depending on the depth of insertion of the finger, facilitating choice of an appropriate depth of insertion by the user depending on size of the finger of the user's own, so as to implement a measurement on blood pressure provided that a feeling of comfort is obtained.

Figure 3:
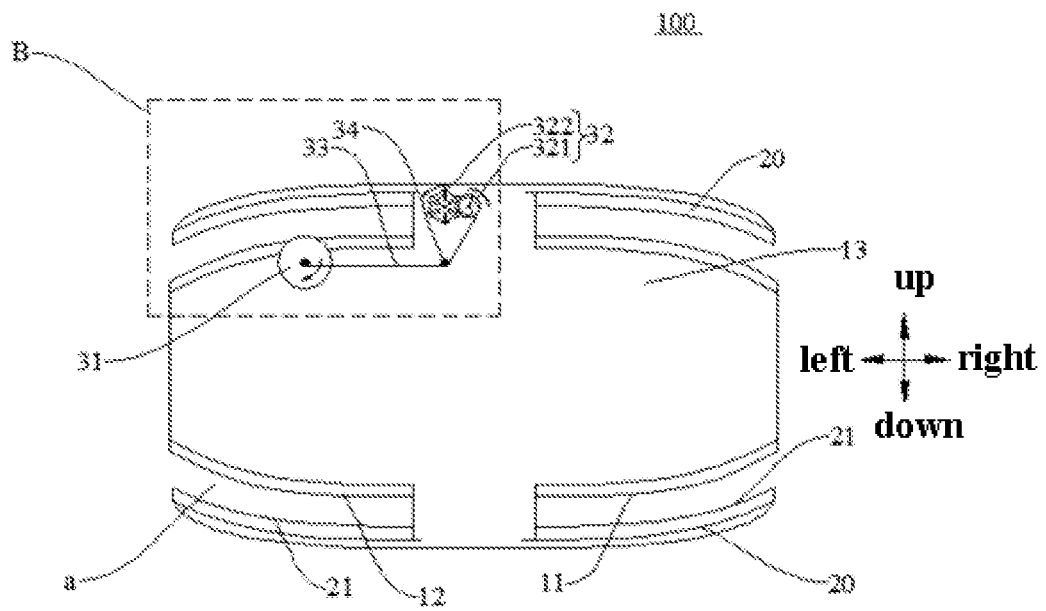
FIG. 3 illustrates a planar view of the blood pressure testing device in an exemplary embodiment of the disclosure.
Figure 4:
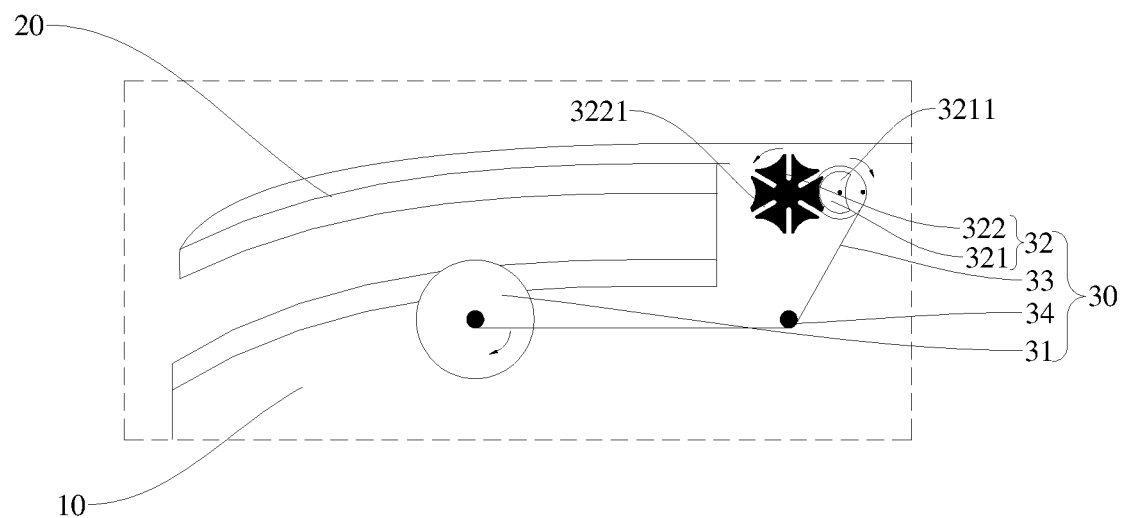
FIG. 4 illustrates an enlarged view of an exemplary embodiment of a region labeled in block 'B' as shown in FIG. 3.

As illustrated in FIG. 3 and FIG. 4, each of the at least one adjusting component 30 comprises a power input element 31, which functions as a power source of motions of the corresponding one of the at least one cover plate 20 and is configured to provide a driving force for lifting up and falling down of the corresponding cover plate 20 once the finger is inserted, by converting insertion motion and/or pulling-out motion of the finger into a specific movement of its own and in turn providing and is also arranged to be mounted, e.g., pivotably, on the housing and further configured to extend at least partially into the testing hole 'a', e.g., depending on condition of insertion and pulling-out of the finger which is subject to the testing so as to be driven to move (e.g., rotate) in one of a first direction and a second direction different from the first direction, depending on whether the finger is removed from or inserted into the testing hole, the first direction being for example a clockwise direction as illustrated in FIG. 3 and the second direction being for example an anticlockwise direction as illustrated in FIG. 3; specifically, in the condition that the power input element 31 is driven to move in the first direction, the corresponding one of the at least one cover plate 20 falls down; and in the condition that the power input element 31 is driven to move in the second direction, the corresponding one of the at least one cover plate 20 lifts up.

More specifically, at least a portion of the power input element 31 extends from the housing to be exposed into the testing hole 'a', such that the power input element 31 may be in direct contact with the finger during a course in which the finger enters and exits the testing hole 'a'; and with the action of the finger, the power input element 31 is pushed to move in the first direction when the finger is inserted into the testing hole 'a' and is pushed to move in the second direction when the finger is removed out of the testing hole 'a'. Thereby, in a condition that the power input element 31 is driven by the finger to be tested, it is advantageous that not only an individual/separate driving unit may not be required so as to simplify a structure of and to decrease a cost of the blood pressure testing device 100, but also the power input element 31 may adjust relative positions of the corresponding one of the at least one cover plate 20 and the finger to be tested relative to each other depending on specific movement of the finger, by adjusting the driving force for lifting up and falling down of the corresponding one of the at least one cover plate 20, such that the corresponding one of the at least one cover plate 20 may be driven to move with a more sensitive and swift response to insertion and removal of the finger, resulting in a more accurate pushing on the finger to be tested.

In embodiments of the disclosure, each of the at least one adjusting component 30 may further comprise an intermittent transmission mechanism 32 which comprises a driving member 321 connected with the power input element 31 and a driven member 322, both the driving member 321 and the driven member 322 cooperating with each other by intermittently forming a separable engagement therebetween to drive the driven member 322 in an intermittent motion, and the driven member 322 being in turn connected with the corresponding one of the at least one cover plate 20 to drive the corresponding one of the at least one cover plate 20 in an intermittent motion synchronously.

Specifically, the power input element 31 is connected with the driving member 321 so as to convert kinetic energy of motions in the first direction or the second direction (which kinetic energy is provided by the finger to be tested) into mechanical energy and then to transfer the mechanical energy to the driving member 321, which kinetic energy is provided by the finger to be tested, hence providing the driving force for lifting up and falling down of the corresponding one of the at least one cover plate 20 once the finger is inserted; and the driving member 321 in turn transfers the mechanical energy intermittently to the driven member 322 by forming the separable engagement therebetween intermittently. As such, during a course in which the driving member 321 transfers the mechanical energy intermittently to the driven member 322, the corresponding one of the at least one cover plate 20 which is connected with the driven member 322 is driven in an intermittent motion synchronously.

Thereby, by providing the intermittent transmission mechanism 32, the corresponding one of the at least one cover plate 20 may for example fall down intermittently during a course in which the finger is inserted into the testing hole 'a' persistently, and/or may for example lift up intermittently during a course in which the finger is removed out of the testing hole 'a' persistently, facilitating that the user adjusts in a reasonable manner the depth of insertion of the finger autonomously in a period in which the corresponding one of the at least one cover plate 20 is stopped temporarily from being pressed down depending on a magnitude of the pressure applied on the finger to be tested, and based on a definite determination by the user whether a feeling of pressure thereof is appropriate, further preventing the finger from being inserted to an excessively large depth in the testing hole 'a' and in turn preventing a resulting excessively large pressure applied on the corresponding one of the at least one cover plate 20 as well as any adverse effect thus caused to results of the detection of the blood pressure testing device 100.

By way of example, the intermittent transmission mechanism 32 is any one of a ratchet wheel transmission mechanism, a Geneva-wheel transmission mechanism (or alternatively referred to as a "sheave wheel transmission mechanism"), and an incomplete gear transmission mechanism. In other words, if only the corresponding one of the at least one cover plate 20 moves intermittently, then any intermittent transmission manner which may provide a sufficient buffer time for lifting up and falling down of the corresponding one of the at least one cover plate 20 may be considered to be an exemplary embodiment of the disclosure.

In a specific embodiment of the disclosure as illustrated in FIG. 3, the intermittent transmission mechanism 32 is for example the sheave wheel transmission mechanism (or Geneva-wheel transmission mechanism) in which both the driving member 321 and the driven member 322 are configured to be rotatable. The driving member 321 is provided with a roller or a deflector rod 3211, and the driven member 322 is provided with a plurality of slots 3221 distributed circumferentially thereon, each of which slots extends radially from the driven member 321, the roller 3211 engaging sequentially with different ones of the plurality of slots 3221 which are arranged continuously circumferentially around the driven member 322 to form sliding fit therebetween so as to push the driven member 322 in an intermittent rotation.

As such, whenever the roller 3211 of the driving member 321 is inserted into one of the plurality of slots of the driven member 322, the driven member 322 where the slot 3221 is located is driven by the roller 3211 to rotate correspondingly a predetermined angle so as to further drive the corresponding one of the at least one cover plate 20 in motion; and then, as the driving member 321 continues to rotate, the roller 3211 sides out of the slot 3221 and thus does not drive the driven member 322 any more, until the driving member 321 rotates a certain angle such that the roller 3211 is inserted into next one of the plurality of slots 3221; at that time, the driven member 322 is further driven in rotation to another predetermined angle correspondingly. As such, not only an intermittent movement of the corresponding one of the at least one cover plate 20 is implemented, but also the movement thereof may be even smoother due to a simple structure and a smooth transmission of the sheave wheel transmission mechanism. Therefore, during use of this blood pressure testing device by the user, the finger to be tested may in turn be subject to a pressure which neither rises sharply nor falls sharply, improving user's experience.

Moreover, by way of example, a time proportion between a movement time and a down time of the intermittent transmission mechanism 32 may be adjusted by setting angles between each two adjacent slots 3221, so as to further adjust specific condition of movement of the corresponding one of the at least one cover plate 20 to control a process of application of the pressure. For example, in a condition that the slots are distributed circumferentially on the driven member in a uniform arrangement, the driven member may be driven by the roller to rotate an identical predetermined angle each time. Alternatively, in a condition that the slots are distributed circumferentially on the driven member in an imperfectly uniform arrangement, the driven member may for example be driven by the roller to rotate a different angle every time.

Continue to refer to FIG. 4, the driving member 321 is for example provided with two rollers 3211 which are distributed in pair symmetrically, the driving member being of a round disc shape, and the two rollers 3211 being formed as a portion of an outer peripheral surface of the driving member 321. Thereby, one of the two rollers 3211 of the driving member 321 may engage and fit with a single one of the slots 3221 of the driven member 322, so as to drive the driven member 322 in motion and to drive in turn the corresponding one of the at least one cover plate 20 to lift up; and the other one of the two rollers 3211 of the driving member 321 may engage and fit with a single one of the slots 3221 of the driven member 322, so as to drive the driven member 322 in motion and to drive in turn the corresponding one of the at least one cover plate 20 to fall down. As such, for the driving member 321 having the two rollers, the time of usage for a single roller 3211 may thus be decreased as compared with a driving member having only one roller, resulting in an even longer service life of the whole intermittent transmission mechanism 32. And due to a relatively compact assembly between the driving member 321 of the round disc shape and the driven member 322 being engaged therewith, an arrangement of the intermittent transmission mechanism 32 becomes even more reasonable and compact.

As illustrated in FIG. 4, each of the at least one adjusting component 30 further comprises a first transmission mechanism 33, through which the driving member 321 and the power input element 31 are connected. The power input element 31 is for example a rotary table as illustrated, and the first transmission mechanism 33 is for example a driving belt as illustrated which is wound at one end thereof on the power input element 31 and wound at the other end thereof on the driving member 321 of the intermittent transmission mechanism, such that the power input element 31 and the driving member 321 move in a same direction with the transmission of the driving belt therebetween.

The power input element 31 drives the driving member 321 in rotation through the first transmission mechanism 33. And in a condition of the winding mode/pattern of the driving belt as illustrated (i.e., the driving belt is wounded in around its rotational axis when the power input member 31 rotates clockwise, as illustrated in FIG. 4), when the power input member 31 rotates in the first direction (i.e., the clockwise direction as illustrated in FIG. 4), the driving member 321 also rotates in the first direction, the roller 3211 located at a lower end of the driving member 321 is in turn inserted into a slot located at a lower end of the driven member 322 to drive the driven member 322 to rotate in the second direction (i.e., the anticlockwise direction as illustrated in FIG. 4), so as to drive the corresponding one of the at least one cover plate 20 to fall down; and when the power input member 31 rotates in the second direction, the driving member 321 also rotates in the second direction, the roller 3211 located at an upper end of the driving member 321 is in turn inserted into a slot located at an upper end of the driven member 322 to drive the driven member 322 to rotate so as to drive the corresponding one of the at least one cover plate 20 to lift up. Thereby, The mechanical energy of the power input element is transferred by the first transmission mechanism 33 to the driving member 321, and then transferred intermittently through the driving member 321 to the driven member 322, so as to drive the corresponding one of the at least one cover plate 20 to fall down or lift up by the rotation of the driven member 322.

Certainly, embodiments of the disclosure may not be limited thereto. For example, by changing specific winding mode/pattern of the driving belt, the power input element 31 and the driving member 321 may move in opposite directions.

As illustrated in FIG. 3 and FIG. 4, each of the at least one adjusting component 30 further comprises a tensioning shaft 34 which is fixedly connected with the housing 10 and pressing against the driving belt normally. Specifically, the tensioning shaft 34 is provided between the power input element 31 and the driving member 321 so as to press tightly against the driving belt. Thereby, by a direction in which the tensioning shaft is tensioned/tightened, a direction in which the power of the power input element 31 is transferred may be changed accordingly, so as to guide the rotation of the driving member 321; and by way of example, by pressing tightly against the driving belt with the tensioning shaft 34, the transfer of the power from the power input element 31 to the driving member 321 may become smoother, so as to enhance working stability of the adjusting component 30.

Figure 5:
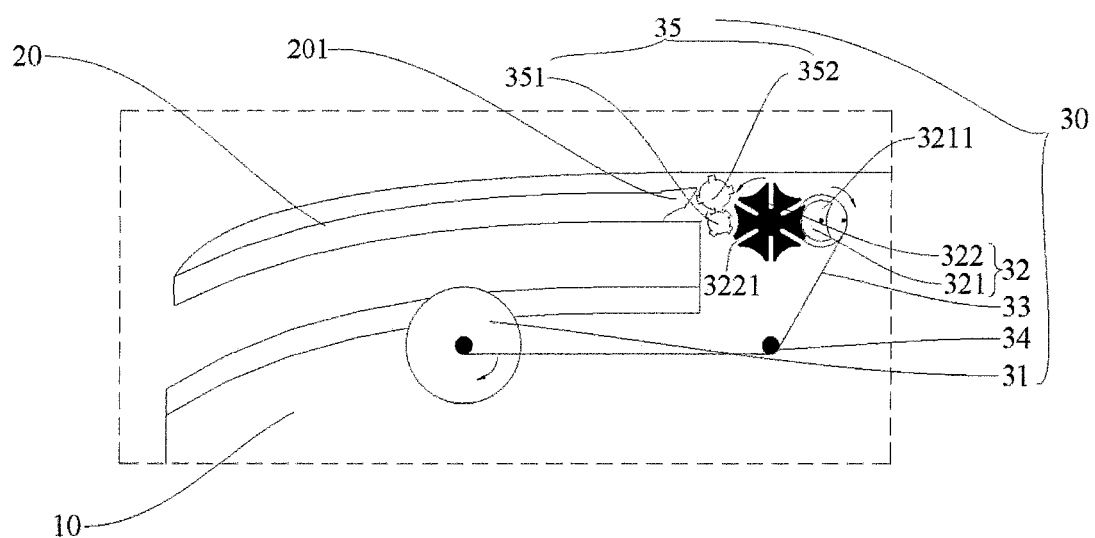
FIG. 5 illustrates an enlarged view of another exemplary embodiment of the region labeled in block 'B' as shown in FIG. 3.

By way of example, as illustrated in FIG. 5, each of the at least one adjusting component 30 further comprises a second transmission mechanism 35, through which the driven member 322 is connected with the corresponding one of the at least one cover plate 20. The second transmission mechanism comprises a first gear wheel 351 and a second gear wheel 352 engaging with each other, the first gear wheel 351 being in a transmittable connection with the driven member 322 of the intermittent transmission mechanism 32, and the second gear wheel 352 being in a transmittable connection with a pivot shaft 201 of the corresponding one of the at least one cover plate 20, around which pivot shaft the corresponding one of the at least one cover plate 20 pivots.

Specifically, the driven member 322 is connected with the first gear wheel 351 so as to drive the first gear wheel 351 in rotation when the driven member 322 rotates, such that the first gear wheel 351 drives the second gear wheel 352 in rotation, and the second gear wheel 352 in turn rotates to drive the pivot shaft 201 engaged therewith to rotate, so as to implement an upward rotation (i.e., lifting up) or a downward rotation (i.e., falling down) of the corresponding one of the at least one cover plate 20 by the pivot shaft. Therefore, by providing the first gear wheel and the second gear wheel which engage with each other, an intermittent movement of the driven member is converted to an intermittent movement of the corresponding one of the at least one cover plate 20, such that the lifting up or falling down of the corresponding one of the at least one cover plate 20 becomes more stable and reliable.

Figure 2:
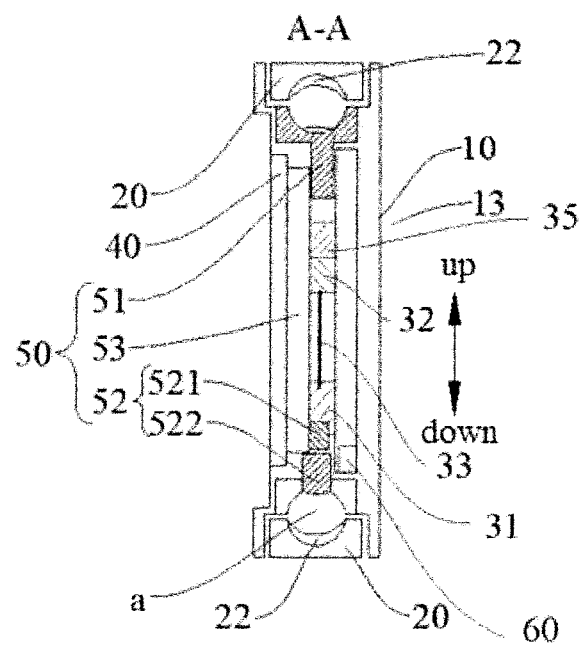
FIG. 2 illustrates a sectional view along a line A-A as shown in FIG. 1.

In a specific embodiment of the disclosure as illustrated in FIG. 2, the housing 10 is provided therein with a mounting chamber 13, in which the first transmission mechanism 33, the second transmission mechanism 35, the intermittent transmission mechanism 32, and a portion of the power input element 31 are all provided. Thereby, the first transmission mechanism 33, the second transmission mechanism 35, the intermittent transmission mechanism 32, and the power input element 31 are mounted within the mounting chamber 13. As a result, not only the blood pressure testing device 100 is more compact in structure thereof and more reasonable in spatial arrangement thereof, but also the first transmission mechanism 33, the second transmission mechanism 35, the intermittent transmission mechanism 32, and the power input element 31 are received and hidden in the housing 10, such that an appearance of the blood pressure testing device 100 is more clean and tidy and aesthetic.

According to embodiments of the disclosure, the testing hole 'a' is provided therein with an elastic member 22 which is connected with the corresponding one of the at least one cover plate 20 at a side thereof facing towards the corresponding one of the at least one detecting element 50. As such, during the use of the blood pressure testing device 100, in a process of the finger to be tested being inserted into the testing hole 'a', the elastic member 22 located at a side of the corresponding one of the at least one cover plate 20 facing towards the corresponding one of the at least one detecting element 50 may for example be stopped elastically against the finger, not only applying a moderate pressure on the finger by the corresponding one of the at least one cover plate 20 so as to apply a more comfortable pressing thereby, but also creating a buffer space between the finger and the cover plate 20, so as to ease or relieve any discomfort of the user, in case that the adjusting component 30 adjusts the relative positions of the cover plate 20 and the finger to be tested excessively and hence the pressure applied on the finger by the cover plate is excessively large.

Moreover, the elastic member 22 is formed by an elastic silicone, or is a PVC spring reed, or is formed by a natural rubber material which is elastic, for example.

In embodiments of the disclosure, the number of the at least one detecting element may be at least three, and the number of the testing holes 'a' may also be at least three. The at least three detecting elements 50 may for example comprise: two detection electrodes 51 configured to detect an electrocardiogram signal respectively and a photoelectric detector 52 configured to detect a pulse signal. And the number of the at least one detecting element is equal to that of the at least one adjusting component, three, each of the at least one detecting element being provided to cooperate with a corresponding one of the at least adjusting component.

During the process of the testing of the blood pressure testing device 100, it is required to capture real-time blood and pulse data at locations of at least three fingers to be tested or at least three sites (locations) to be tested, so as to measure and determine both pressure data and pulse data of the user. As a result, within the at least three testing holes 'a', there are at least three (e.g., identical number of) detecting elements 50, such that both the pulse and the blood pressure of the user may be measured, e.g., by three detecting elements 50 within corresponding three detecting holes 'a'.

In other words, for example, in the at least three detecting elements 50, two detecting elements 50 are detection electrodes 51 configured to measure the pressure data of the user by a potential difference between the two detection electrodes 51, and the potential difference therebetween essentially being a data difference between a high pressure peak value and a low pressure peak value; furthermore, the other one of the at least three detecting elements 50 is a photoelectric detector 52 configured to detect the pulse signal. The photoelectric detector 52 for example senses a variation in blood vessel diameter at locations being detected, of the user, and records it as one pulse-beat, and in turn records the number of beats of pulse of the user per unit time, so as to measure the pulse of the user.

In summary, by providing at least the two detection electrodes 51 and the photoelectric detector 52 within corresponding testing holes 'a', not only the blood pressure and the pulse of the user may be measured in real time and quickly, but also the results of the detection of the blood pressure testing device 100 may be more accurate.

In specific embodiments as illustrated in FIG. 3 and FIG. 4, the number of the detection electrodes 51 is for example three, and the number of the photoelectric detector is for example one; and by individual and separate adjusting components 30, movement of each cover plate 20 corresponding to each detection electrode 51 is controlled, respectively.

Furthermore, as illustrated in FIG. 2 and FIG. 3, a corresponding one of the testing holes 'a' provided at each of the detection electrodes 51 comprises: a first chute 21 (i.e., movable chute) formed on the corresponding one of the at least one cover plate 20, and a second chute 11 formed on the detection electrode 51 (i.e., the second chute is a fixed chute for the detection electrode), the first chute 21 and the second chute 11 being provided opposite to each other. And a corresponding one of the testing holes 'a' provided at the photoelectric detector 52 comprises: a first chute (i.e., movable chute) 21 formed on the corresponding one of the at least one cover plate 20, and a third chute 12 with a portion thereof being formed on the housing 10 and the other portion thereof being formed on the photoelectric detector 52 (i.e., the third chute is a fixed chute for the photoelectric detector), the first chute 21 and the third chute 12 being provided opposite to each other.

In other words, each detection electrode 51 and a corresponding second chute 11 are for example formed integrally, and the photoelectric detector 52 extends to be in contact with a wall of a corresponding second chute 11 or a corresponding third chute 12, and in turn to abut at the wall against an external side of the finger to be detected, i.e., a side of the finger facing away from the other side thereof which has a fingerprint thereon), such that the blood pressure testing device 100 abut more tightly against the finger to be tested, and in turn obtains a more accurate result of detection, and the first chute 21 and the second chute 11 cooperate with each other to define a space in and out of which the finger may move, or the first chute 21 and the third chute 12 cooperate with each other to define a space in and out of which the finger may move, thus providing a guiding effect for insertion and removal of the finger to be tested.

Specifically, as illustrated in FIG. 2, the photoelectric detector 52 comprises a light-induction chip 521 and a light guide column 522. Light rays emitted by the light-induction chip 521 may be transferred through the light guide column 522 into the corresponding testing hole 'a', and then projected onto the finger to be tested so as to acquire pulse data. And a circuit board 53 is provided within the housing, with which circuit board both the detection electrodes 51, and the light-induction chip 521 of the photoelectric detector 52 are connected electrically.

In specific embodiments as illustrated in FIG. 1 and FIG. 3, the housing 10 and the corresponding one of the at least one cover plate 20 cooperate with each other to form a substantially cuboid shaped structure, and the testing holes 'a' are provided at both side ends in a longitudinal (i.e., lengthwise) direction of the cuboid shaped structure, respectively, with two testing holes 'a' which are located therein at an identical side end being provided symmetrically in a width direction of the cuboid shaped structure, for example; and the testing holes 'a' all extend inwards from outside to deviate gradually from a central axis in the longitudinal direction of the cuboid shaped structure. Specifically, for example, there are two testing holes 'a' which are provided to face away from each other at both side ends at an upper portion of the blood pressure testing device 100; and for example, there are also two testing holes 'a' which are provided to face away from each other at both side ends at a lower portion of the blood pressure testing device 100.

As such, the housing 10 and each of the cover plates 20 cooperate with each other to define collectively a structure of a substantially cuboid shape, facilitating holding the blood pressure testing device 100 by hand, and during the use, the testing holes 'a' provided at both left and right side ends at the upper portion of the housing 10 and at both left and right side ends at the lower portion of the housing 10 may for example be inserted by corresponding fingers, e.g., testing holes 'a' at left side ends may be inserted by both thumb and index finger of the left hand of the user, testing holes 'a' at right side ends may be inserted by both thumb and index finger of the right hand of the user. As a result, the blood pressure testing device 100 is designed to meet requirement of a structure of human body mechanics, such that the use thereof is simpler and convenient.

Moreover, the blood pressure testing device 100 further comprises a display component 40 and a control element 60. The control element 60 is arranged to be connected electrically with the at least one detecting element 50, and configured to receive the electrocardiogram signal and the pulse signal generated by detection of the at least one detecting element 50; and the display component 40 is arranged to be fixedly connected on the housing 10 and configured to be electrically connected with the control element 60 so as to output blood pressure information.

Specifically, the control element may for example be configured to receive both the pulse signal and the electrocardiogram signal from the at least one detecting element 50, and in turn to control the display component 40 to display visually number of beats of pulse and a high pressure peak value data and a low pressure peak value data all converted from the pulse signal and the electrocardiogram signal which are received, by calculation of the control element 60 connected with the display component, to the user. As such, not only it is facilitated that the user reads relevant data visually and intuitively, but also the blood pressure testing device 100 is small in its volume and thus is easy to carry and is also immediately ready for use.

A blood pressure testing method according to embodiments of the disclosure is sketched in brief as below: hardware for implementing such a method is set up based on a non-intrusive method for detection of blood pressure with both photoplethysmography (PPG) signal and electrocardiograph (ECG) signal and then calibrated by a systematic algorithm so as to output values of arterial blood pressure (ABP). And a pulse signal may be obtained by detecting variation in magnitude of blood vessel diameter at locations of a hand of the user, with the light-induction chip 521; and an electrocardiogram signal may also be obtained by detecting a variation of difference in capacitance between or among detection electrodes 51. Then, both blood pressure and pulse data as detected by the blood pressure device 100 may in turn be displayed visually by the display component 40.

In embodiments of the disclosure, unless being explicitly specified and defined in the context otherwise, terminologies such as "mount", "connect", "connect(ed) . . . with", "fixed" and the like are intended to be inclusive and should thus be comprehended in a broad sense, e.g., may be interpreted as fixed connection or detachable connection, or even integrated; and may be a mechanical connection, or an electrical connection, or communication with each other or one another; and may be direct connection, or indirection connection via an intermediate medium, or an internal communication between two elements, or even an interaction relationship between two elements. As to those skilled in the art, specific meanings of above terminologies in embodiments of the disclosure may be comprehended according to specific context herein.

In embodiments of the disclosure, unless being explicitly specified and defined in the context otherwise, a first feature being "above" or "below" a second feature may contain meanings comprising: the first feature and the second feature being in direct contact; or the first feature and the second feature being in contact via another feature disposed therebetween, rather than being in direct contact. Moreover, the first feature being "above", "over" and "on" may contain a meaning of the first feature being directly/right over or inclined over the second feature, or may only represent that the first feature has a level (or a height from horizontal) higher/larger than that of the second feature. The first feature being "below", "under", "beneath" the second feature may contain a meaning of the first feature being directly/right under or inclined under the second feature, or may only represent that the first feature has a level (or a height from horizontal) lower/smaller than that of the second feature.

In depictions herein, description referring to terminologies such as "an embodiment", "embodiments", "example", "specific example" or "examples" may mean that specific feature(s), structure(s), material or characteristics in combination therewith may be contained within at least one embodiment or example of the disclosure. In the description, illustrative expressions concerning above terminologies may not necessarily refer to same embodiment(s)/example(s). Furthermore, specific feature(s), structure(s), material or characteristics as depicted may be combined mutually in any one or more of embodiments or examples appropriately. In addition, it may occur to those skilled to join and combine different embodiments or examples as depicted herein.

There are several advantageous technical effects brought about by the technical solutions as provided in embodiments of the disclosure, as below:

The blood pressure testing device is provided as above in embodiments of the disclosure, such that: when a finger is inserted into a corresponding one testing hole, a corresponding adjusting component may force a corresponding cover plate to move towards the adjusting component such that the testing hole is shrunken/decreased so as to compress against the finger tightly, not only facilitating a detection on blood pressure and pulse by the blood pressure testing device without pressing for a long time in the process of the detection and in turn enhancing experience of testing, but also resulting in a simple operation, a more uniform distribution of force applied on the finger, and more accurate testing results during acquisition of signals by the detecting element(s).

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle.

Although the disclosure is described in view of the attached drawings, the embodiments disclosed in the drawings are only intended to illustrate the preferable embodiment of the present disclosure exemplarily, and should not be deemed as a restriction thereof.

Although several exemplary embodiments of the general concept of the present disclosure have been shown and described, it would be appreciated by those skilled in the art that various changes or modifications may be made in these embodiments without departing from the principles and spirit of the disclosure and lie within the scope of present application, which scope is defined in the claims and their equivalents.

As used herein, an element recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

What is claimed is:

1. A blood pressure testing device for a finger, comprising:
a housing;

at least one cover plate connected pivotably to the housing;

at least one detecting element, each of which is configured to detect an electrocardiogram signal and a pulse signal, and arranged to be accommodated within and connected with the housing and provided opposite to corresponding one of the at least one cover plate so as to cooperate to define collectively a testing hole therebetween; and at least one adjusting component, each of which is arranged to be connected with the corresponding one of the at least one cover plate, and configured to drive the corresponding one of the at least one cover plate to carry out one of the operations comprising: lifting up to move away from a corresponding one of the at least one detecting element, and falling down to approach the corresponding one of the at least one detecting element, wherein the number of the at least one detecting element is at least three, and the number of the testing holes is also at least three, and wherein each of the at least one adjusting component further comprises: an intermittent transmission mechanism comprising a driving member connected with the power input element and a driven member, both the driving member and the driven member cooperating with each other by intermittently forming a separable engagement therebetween to drive the driven member in an intermittent motion, and the driven member being connected with the corresponding one of the at least one cover plate to drive the corresponding one of the at least one cover plate in an intermittent motion synchronously.

2. The blood pressure testing device according to claim 1, wherein each of the at least one adjusting component is configured to carry out one of operations comprising:

driving the corresponding one of the at least one cover plate to fall down gradually as the finger is inserted into the testing hole, before being tested; and driving the corresponding one of the at least one cover plate to lift up gradually as the finger is removed from the testing hole, after being tested.

3. The blood pressure testing device according to claim 2, wherein each of the at least one adjusting component comprises a power input element, which functions as a power source configured to provide power for driving motions of the corresponding one of the at least one cover plate and is arranged to be mounted to the housing and to extend at least partially into the testing hole, and is configured to be driven to move in one of a first direction and a second direction different from the first direction depending on whether the finger is removed from or inserted into the testing hole, and wherein in the condition that the power input element is driven to move in the first direction, the corresponding one of the at least one cover plate falls down; and in the condition that the power input element is driven to move in the second direction, the corresponding one of the at least one cover plate lifts up.

4. The blood pressure testing device according to claim 1, wherein the intermittent transmission mechanism is one of a ratchet wheel transmission mechanism, a Geneva-wheel transmission mechanism, and an incomplete gear transmission mechanism.

5. The blood pressure testing device according to claim 4, wherein the intermittent transmission mechanism is the Geneva wheel transmission mechanism in which both the driving member and the driven member are configured to be rotatable; and wherein the driving member is provided with a roller and the driven member is provided with a plurality of slots distributed circumferentially thereon, each of which extends radially from the driven member, the roller engaging sequentially with different ones of the plurality of slots which are arranged continuously circumferentially around the driven member to form sliding fit therebetween so as to push the driven member in an intermittent rotation.

6. The blood pressure testing device according to claim 5, wherein the driving member is provided with at least one pair of rollers which are distributed symmetrically, the driving member being of a round disc shape, and the rollers being formed as a portion of an outer peripheral surface of the driving member.

7. The blood pressure testing device according to claim 1, wherein each of the at least one adjusting component further comprises a first transmission mechanism, through which the driving member and the power input element are connected.

8. The blood pressure testing device according to claim 7, wherein the power input element is a rotary table, and the first transmission mechanism is a driving belt which is wound on the power input element at one end thereof and wound on the driving member of the intermittent transmission mechanism at the other end thereof, and configured to be driven by the power input element and in turn to drive the driving member such that the driving member implements one of a movement in a same direction relative to the power input element and a movement in an opposite direction relative to the power input element.

9. The blood pressure testing device according to claim 8, further comprising a tensioning shaft which is fixedly connected with the housing and pressing against the driving belt normally.

10. The blood pressure testing device according to claim 7, wherein each of the at least one adjusting component further comprises a second transmission mechanism, through which the driven member is connected with the corresponding one of the at least one cover plate.

11. The blood pressure testing device according to claim 10, wherein the second transmission mechanism comprises a first gear wheel and a second gear wheel engaging with each other, the first gear wheel being in a transmittable connection with the driven member of the intermittent transmission mechanism, and the second gear wheel being in a transmittable connection with a pivot shaft of the corresponding one of the at least one cover plate, around which pivot shaft the corresponding one of the at least one cover plate pivots so as to implement one of lifting up and falling down.

12. The blood pressure testing device according to claim 10, wherein the housing is provided therein with a mounting chamber, in which the first transmission mechanism, the second transmission mechanism, the intermittent transmission mechanism, and a portion of the power input element are all provided.

13. The blood pressure testing device according to claim 1, wherein the testing hole is provided therein with an elastic member which is connected with the corresponding one of the at least one cover plate at a side thereof facing towards the corresponding one of the at least one detecting element.

14. The blood pressure testing device according to claim 1, wherein the number of the at least one detecting element is three, comprising: two detection electrodes configured to detect the electrocardiogram signal respectively and a photoelectric detector configured to detect the pulse signal; and wherein the number of the at least one adjusting component is also three, each of which being provided to cooperate with a corresponding one of the at least detecting element.

15. The blood pressure testing device according to claim 14, wherein a corresponding one of the testing holes provided at each of the detection electrodes comprises: a first chute formed on the corresponding one of the at least one cover plate, and a second chute formed on the detection electrode, the first chute and the second chute being provided opposite to each other; and wherein a corresponding one of the testing holes provided at the photoelectric detector comprises: a first chute formed on the corresponding one of the at least one cover plate, and a third chute with a portion thereof being formed on the housing and the other portion thereof being formed on the photoelectric detector, the first chute and the third chute being provided opposite to each other.

16. The blood pressure testing device according to claim 1, wherein the housing and the corresponding one of the at least one cover plate cooperate with each other to form a substantially cuboid shaped structure, and the testing holes are provided at both side ends in a longitudinal direction of the cuboid shaped structure, respectively, with two testing holes therein at an identical side end being provided symmetrically in a width direction thereof; and the testing holes all extend inwards from outside to deviate gradually from a central axis in the longitudinal direction of the cuboid shaped structure.

17. The blood pressure testing device according to claim 1, further comprising:

a control element, which is arranged to be connected electrically with the at least one detecting element, and configured to receive the electrocardiogram signal and the pulse signal generated by detection of the at least one detecting element; and a display component, which is arranged to be fixedly connected on the housing and configured to be electrically connected with the control element so as to output blood pressure information.

* * * * *